United States Patent [19]
Mueller

[11] Patent Number: 5,807,384
[45] Date of Patent: Sep. 15, 1998

[54] TRANSMYOCARDIAL REVASCULARIZATION (TMR) ENHANCED TREATMENT FOR CORONARY ARTERY DISEASE

[75] Inventor: Richard L. Mueller, Sunnyvale, Calif.

[73] Assignee: Eclipse Surgical Technologies, Inc., Sunnyvale, Calif.

[21] Appl. No.: 771,794

[22] Filed: Dec. 20, 1996

[51] Int. Cl.$^6$ .................................................. A61B 17/36
[52] U.S. Cl. ................................ 606/7; 606/15; 600/16; 128/898
[58] Field of Search ............................ 606/7, 9, 14–15; 604/4, 174–175; 600/16; 128/898; 623/3

[56] References Cited

U.S. PATENT DOCUMENTS

| | | | |
|---|---|---|---|
| 4,955,856 | 9/1990 | Phillips | 623/3 |
| 4,995,857 | 2/1991 | Arnold | 600/16 |
| 5,135,467 | 8/1992 | Citron | 600/16 |
| 5,147,388 | 9/1992 | Yamazaki | 600/16 |
| 5,190,058 | 3/1993 | Jones et al. | 128/898 |
| 5,275,580 | 1/1994 | Yamazaki | 623/3 |
| 5,409,019 | 4/1995 | Wilk | 600/16 |
| 5,429,144 | 7/1995 | Wilk | 28/898 |
| 5,533,957 | 7/1996 | Aldea | 600/16 |
| 5,655,548 | 8/1997 | Nelson et al. | 128/898 |

OTHER PUBLICATIONS

Deckelbaum, "Cardiovascular Apps. of Laser Tech.", Lasers in Surgery and Medicine, 15:315–341 (1994).

Benetti et al, "Video–Assisted Coronary Bypass Surgery", J. Card. Surg., 10:620–625 (1995).

(List continued on next page.)

*Primary Examiner*—Francis Jaworski
*Attorney, Agent, or Firm*—Ray K. Shahani; Janet Kaiser Castaneda; Christopher N. Sears

[57] ABSTRACT

A transmyocardial revascularization (TMR) enhanced treatment for coronary artery disease and other medical procedures utilizing a source of laser energy and a laser delivery means attached thereto, the treatment or other medical procedure being one in which the coronary artery is temporarily occluded during a surgical procedure, the enhanced treatment comprising the steps of positioning the laser delivery means adjacent the distal anatomy of the heart muscle, delivering laser energy to the distal anatomy of the heart muscle through the laser delivery means to create at least one TMR channel communicating oxygenated blood from the left ventricle to myocardium of the distal anatomy of the heart muscle, such that during treatment or other medical procedure in which the coronary artery is temporarily occluded, the distal anatomy of the heart is essentially continuously supplied with oxygenated blood, and performing the treatment or other medical procedure in which the coronary artery is temporarily occluded during a surgical or other procedure. A device for TMR enhanced treatment of coronary artery disease and other medical procedures in which the coronary artery is temporarily occluded during a surgical procedure, the device having first tubular means communicating oxygenated blood in the left ventricle with the device, second tubular means for perfusing oxygenated blood directly into myocardium in the distal anatomy of the heart muscle, and fluid communication means for communicating oxygenated blood between the first tubular means and the second tubular means. In preferred embodiments, both the first and the second tubular means have sharpened distal ends for mechanically piercing tissue of the heart muscle, and the second tubular means has at least one perfusion aperture on the sidewall adjacent the distal end of the tubular means. Additionally, a pump means for pumping oxygenated blood through the TMR device is disclosed, the pump means to be actuated either manually or automatically, and optionally repeated at a specific rate during the treatment or other medical procedure. The treatment or other medical procedure includes, and is not limited to, coronary artery angioplasty, coronary artery bypass grafting (CABG), and minimally invasive direct coronary artery bypass grafting (MIDCAB).

33 Claims, 10 Drawing Sheets

OTHER PUBLICATIONS

Saatvedt et al., "Transmyocardial Laser Revascularization & Coronary Artery Bypass W/O Cardiopulmonary Bypass" Annals of Thoracic Surgeons, vol. 62, pp. 323–324, Jul. 1996.

Mirhoseini et al., "Transmyocardial Laser Revascularization as a Combined Procedure and a Sole Therapy: Ten Year Clinical Experience", Lasers in Surgery & Medicine, Suppl. 7, 1995, p. 10.

Mirhoseini et al., "Coronary Artery Bypass in Conjunction with Transmyocardial Laser Revascularization," presented at the American Society for Laser Medicine & Surgery Meeting, Apr. 1996.

Soatvedt, K. et al, "TMLR Adjacent to CABG w/o CPB" *Abstract* presented at TMLR Symposium Texas Heart Institute at San Diego, Ca., Apr. 27, 1996.

Mirhoseini, M. et al, "Coronary Artery Bypass in Conjunction w/ TMLR", *Abstract* ASLMS meeting Apr. 14–18, 1996 Orlando, Fl.

Mirhoseini, M. "Historical Perpective: TM Laser Revascularization" *Abstract*; presented at TMLR Symposium Texas Heart Inst., San Diego, Ca., Apr. 27, 1996.

Trehon, N. "TMLR as an Adjacent to CABG", *Abstract*, presented at TMLR Symposium, Texas Heart Institute , San Diego, Ca., Apr. 27, 1996.

Trehon, N. et al "Complete MR with TL as an Adjuct to CABG without Cardiopulmonary Bypass", *Abstract*, presented at Amer. College of Cardiology 46th Annual Scientific Session, Anaheim, Ca., Mar. 17, 1997.

Trehan, N. et al "TMLR as an Adjuct to CABG", Indian Heart Journal Jul.–Aug. 1996.

TRANSMYOCARDIAL REVASCULARIZATION (TMR) ENHANCED TREATMENT FOR CORONARY ARTERY DISEASE

FIELD OF THE INVENTION

The present invention relates generally to apparatus and methods for enhancing coronary artery disease treatment. More particularly, the invention relates to apparatus and methods for transmyocardial revascularization (TMR) enhanced minimally invasive direct coronary bypass (MIDCAB) procedures.

BACKGROUND OF THE INVENTION

Coronary Artery Disease

Heart disorders are a leading cause of death in developed countries. Such disorders also impair the quality of life of millions of people by restricting activity because of pain, breathlessness, fatigue, fainting spells and anxiety. The major cause of heart disease in developed countries is impaired blood supply. One cause of reduced blood supply to the heart is coronary artery disease.

FIG. 1 is a schematic view of the coronary arteries on the outer surface of the human heart. Though the heart supplies blood to all other parts of the body, the heart itself has relatively little communication with the oxygenated blood supply. Thus, the coronary arteries essentially comprised of the right anterior descending (RAD) coronary artery 100, the left anterior descending (LAD) coronary artery 102 and the circumflex (CIR) coronary artery 103 arise from the aorta 104 beneath the aortic arch 106. The coronary arteries encircle the heart muscle on either side "like a crown" to supply the heart itself with blood.

Coronary artery disease generally involves and results in a narrowing of the coronary arteries due to atherosclerosis. The resulting ischemia or blockage can lead to angina pectoris, a pain in the chest, shoulders, arms or jaw due to a lack of oxygen to the heart, or infarction, death of an area of the myocardium caused by the ischemia.

Coronary artery blockage can be relieved in a number of ways, including drug therapy, utilization of nitrates, beta-blockers, and peripheral vasodilatator drugs (to dilate the arteries) and thrombolytic drugs (to dissolve the clot). Transluminal angioplasty is often indicated —the narrowed part of the artery, clogged with atherosclerotic plaque or other deposits, can be stretched apart by passing a balloon to the site and gently inflating it a certain degree. Additionally, stents or other tubular structures can be implanted during angioplasty to hold the walls of a vessel apart. Risks attendant with angioplasty include blockage of the coronary arteries essentially completely during the time the balloon is being placed and expanded, and also the possibility that portions of the atherosclerotic material can become dislodged which may cause a total blockage at a point downstream of the subject occlusion thereby requiring emergency procedures.

CABG

Coronary artery bypass grafting (CABG) is a procedure in which the coronary arteries are bypassed for delivering oxygenated blood to myocardium. CABG is the most common and successful major heart operation performed with over 500,000 procedures being performed annually in the United States alone. CABG may be performed as a sternotomy procedure, or more recently, as a MIDCAB procedure (see below). In a sternotomy, a surgeon makes a sternotomy incision down the center of the patient's chest and the heart is exposed by opening the pericardium. A length of vein is removed from another part of the body, typically the leg. The patient is connected to a heart-lung machine which takes over the function of the heart and lungs during the operation. The section of vein is first sewn to the aorta and then sewn onto a coronary artery at a place such that oxygenated blood can flow directly into the heart. Not only does the procedure typically require the installation of the heart-lung machine but the sternum must be sawed through and the risk of infection is enhanced during the time the chest cavity is spread open.

The use of the cardiopulmonary bypass (CPB) machine has become standard for CABG and other procedures because the beating heart can typically tolerate only about one minute of blood flow interruption before the distal anatomy of the heart reacts to the lack of oxygenated blood and the risk of heart ischemia or infarction increases. The CPB machine takes over the heart's function of pumping oxygenated blood through the rest of the body during surgical intervention, typically 20 minutes up to several hours in duration.

FIG. 2 is a representative schematic view of the use of a cardiopulmonary bypass (CPB) machine. At any suitable point in the vasculature, typically the femoral vein 130, percutaneous communication via "blood out" line 132 permits blood to flow from the vein 130 to the bypass pump 134 of the CPB machine 130. The pump 134 transfers the blood to an oxygenator module 136, from which the blood is circulated back to the patient via "blood in" line 140. Re-entry is to another suitable point in the vasculature, such as the femoral artery 142. Once this flow pattern is established, it is safe to apply a clamp means 144 across the aorta 104 and proceed with the operation required. Protection of the heart, then, is carried out by arresting electrical and mechanical activity in the heart by several methods. These include thermal chilling of the heart to slow its metabolic rate and injecting cardioplegia drugs or other substances 146. This need to "preserve" the heart is a complicating factor in CPB.

Other drawbacks exist in the use of CPB equipment. Placing a patient on a bypass machine has an approximately 2% to 3% complication rate. As an example of one of the complications, the rollers of the typically peristaltic pumps used in the procedure often damage red blood cells. Thus the body becomes burdened with the need to flush out and recover from the accumulation of these dead, ruptured cells and cellular debris which would otherwise accumulate in the various capillary beds, veins, etc. Further complications include strokes, loss of memory, blood clotting, etc.

U.S. Pat. No. 5,429,144 issued Jul. 4, 1995 to Wilk teaches an alternative coronary artery bypass method. This patent teaches the use of a stent wherein the stent is disposed within the myocardium during a beating heart procedure. The stent may extend only partially through myocardium and may terminate at either end in the left ventricle, a coronary artery, or both. It is an object of the patent to establish a permanent flood flow path from either the left ventricle or from a coronary artery into myocardium, in any case at a point downstream of a vascular obstruction. However, risks attendant with this procedure include migration or movement of the stent due to the constantly contracting and expanding heart muscle.

MIDCAB

A minimally invasive direct coronary artery bypass (MIDCAB) procedure, an alternate way to revascularize the coronary vessels using arterial conduits without extracorporeal circulation, has recently been described. FIG. 3 is a representative drawing showing typical locations of sternotomy and thoracotomy incisions. It will be understood that the present invention includes use of these and other incision locations, including laparotomy, etc. MIDCAB procedures replace the traumatic vertical sternotomy incision 160, as described above, with a shorter, more horizontal thoracotomy incision 162 to work on the still beating heart. No CPB equipment is needed. A recent article entitled *Video Assisted Coronary Bypass Surgery* by Benetti, et al., J. Card. Surg., 10:620–625 (1995) describes a MIDCAB in which a thoracotomy exposes the heart over the fifth left intercostal space. Using a thorascope in the thorax to enhance visualization via video signal, portion of the left internal mammary artery (LIMA) is harvested and grafted directly to the left anterior descending (LAD) coronary artery 102. The same procedure can be performed on the right side using the RIMA and the RAD 100, in the center for treating blockages of the circumflex coronary artery 103, or otherwise.

A continuing drawback of the MIDCAB procedure is that the distal portions of the heart are still left without a blood supply for a significant period of time, generally for a minimum of between 5 and 15 minutes, during which time the coronary artery is blocked or clamped, the incision is made in the coronary artery and the distal end of the graft is sewed in place. Generally, before or at the time an incision is made in the coronary artery itself, blood flow through the artery must be arrested using pressure, suction or a silastic band or clamp, or by placing stay sutures proximal to the bypass site and tightening the sutures to provide a dry field. Even if performed successfully, the distal anatomy of the heart often is oxygen starved during the procedure itself.

TMR

In the treatment of heart disease, one method of improving myocardial blood supply, particularly to distal portions of the heart, is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

Recent surgical and minimally invasive surgical (MIS) TMR studies have been performed using laser energy to form a number of channels through the epicardium, myocardium, and endocardium to allow blood from the ventricle to perfuse the channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent. In any event, such TMR channels supply blood to the distal portion of the heart when the coronary arteries are impaired and unable to do so. CAB procedures alone may improve vascularization, but in many cases such procedures are unable to correct for distal lesions. TMR solves this problem.

There exists a need, therefore, to provide an adjunct and supplemental therapy, such as TMR, to CABG or MIDCAB procedures to reduce or eliminate the risk of starving the distal heart anatomy during the placement of CAB grafts and to supplement CAB grafts which may not otherwise adequately resupply the heart muscle with sufficient oxygenated blood.

ADVANTAGES AND SUMMARY OF THE INVENTION

Thus, it is an advantage of the present invention to provide a method and apparatus for performing CABG or MIDCAB heart surgery on a beating heart which overcome the disadvantages of the prior art.

It is a further advantage of the present invention to teach the use of TMR as an adjunct therapy to treatment of coronary artery disease, including angioplasty, CABG and MIDCAB, to reduce or eliminate the risk of starving the distal heart anatomy of oxygen during the treatment.

It is a further advantage of the present invention to create a plurality of TMR channels in the vicinity of distal heart anatomy for communicating oxygenated blood from the ventricle directly to myocardium in that area to reduce or eliminate the risk of starving the distal heart anatomy of oxygen during angioplasty and the placement of CAB grafts.

It is a further advantage of the present invention to provide a TMR device for communicating oxygenated blood directly to myocardium to reduce or eliminate the risk of starving the distal heart anatomy of oxygen during treatment.

Another advantage of the present invention is to use TMR as a long term supplement to coronary artery bypass heart surgery, and not as just an adjunct therapy thereto.

Another advantage of the present invention is to use TMR to increase the available channels and demand paths for the new coronary artery connection and supply.

It is a further advantage of the present invention to trigger, stimulate or otherwise cause the body to react to increased demand by increasing blood supply or by angiogenesis (growth of new vessels).

It is a further advantage of the present invention to trigger, stimulate or otherwise cause the body to react to coincide with the new blood supply to maximize the potential for rapid angiogenesis.

Therefore, in summary, the present invention is a method for supplying blood to heart muscle during a procedure of the type performed on a beating heart where at least one coronary artery is temporarily occluded. The method comprises the following steps: positioning a tool adjacent at least a portion of the heart muscle likely to be deprived of a blood supply while the at least one coronary artery is temporarily occluded; creating at least one channel communicating oxygenated blood from a heart chamber to myocardium of the portion of the heart muscle, such that during the treatment or other medical procedure in which the coronary artery is temporarily occluded, the portion of the heart is essentially continuously supplied with oxygenated blood; and performing the treatment or other medical procedure in which the at least one coronary artery is temporarily occluded. The tool can be a laser delivery means, mechanical cutting means, radio-frequency or ultrasound device, and the step of creating at least one channel comprises delivering laser or ultrasound energy to or mechanically creating an opening in the portion of the heart muscle to create a transmyocardial revascularization channel extending into a left ventricle of the heart.

The medical procedure can be a coronary artery angioplasty and TMR can be used as a temporary distal anatomy bypass thereby allowing longer duration primary vascular intervention. Additionally, the treatment or other medical procedure can be a coronary artery bypass grafting (CABG) or a minimally invasive direct coronary artery bypass grafting (MIDCAB). At least one TMR channel can be initiated at an epicardial surface or an endocardial surface. The laser delivery means further comprises a piercing tip and the step of positioning the laser delivery means adjacent the portion of the heart muscle is replaced with either the step of mechanically piercing an endocardial surface and positioning the laser delivery means inside myocardium comprising the portion of the heart muscle, or the step of mechanically piercing an epicardial surface and positioning the laser delivery means inside myocardium comprising the portion of the heart muscle.

A device for transmyocardial revascularization (TMR) enhanced treatment of coronary artery disease and other medical procedures is also disclosed herein, the treatment or other medical procedure being one in which at least one coronary artery is temporarily occluded during a surgical or MIS procedure. The device comprises, in combination, perfusion tube means for extending from a heart chamber into myocardium of the heart muscle, the perfusion tube means having fluid communication means for communicating oxygenated blood from the heart chamber directly into myocardium, such that during treatment or other medical procedure in which the at least one coronary artery is temporarily occluded, myocardium of the heart muscle is essentially continuously supplied with oxygenated blood. The fluid communication means could be at least one perfusion aperture disposed adjacent a distal end of the perfusion tube means. The perfusion tube means could have a sharpened distal end for mechanically piercing tissue of the heart muscle. Another device for transmyocardial revascularization (TMR) enhanced treatment of coronary artery disease and other medical procedures is also disclosed, the treatment or other medical procedure being one in which at least one coronary artery is temporarily occluded during a surgical procedure. The device comprises, in combination, tubular inlet means extending from and communicating oxygenated blood from a heart chamber to the device, tubular outlet means for perfusing oxygenated blood directly into myocardium of the heart muscle, and fluid communication means for communicating oxygenated blood between the tubular inlet means and the tubular outlet means for perfusing oxygenated blood directly into myocardium of the heart muscle, such that during treatment or other medical procedure in which the at least one coronary artery is temporarily occluded, the distal anatomy of the heart is essentially continuously supplied with oxygenated blood. The fluid communication means can be at least one perfusion aperture through the tubular outlet means adjacent a distal end of the tubular outlet means. The tubular inlet means and the tubular outlet means can have a sharpened distal end for mechanically piercing tissue of the heart muscle. The communication means for communicating oxygenated blood between the tubular inlet means and the tubular outlet means can comprise a manifold connected therebetween having at least one inlet for oxygenated blood and having at least one outlet for oxygenated blood. The manifold can further comprise a pump means for pumping oxygenated blood from the at least one oxygenated blood inlet through the at least one oxygenated blood outlet. The pump means can be actuated manually.

An enhanced treatment for coronary artery disease and other medical procedures utilizing a perfusion tube extending from the left ventricle into myocardium of the heart muscle, is also disclosed. The perfusion tube has fluid communication means for communicating oxygenated blood from the left ventricle directly into myocardium, the treatment or other medical procedure being one in which a coronary artery is temporarily occluded during a surgical, MIS or percutaneous procedure. The enhanced treatment comprises the following steps, in combination: creating at least one pathway for communicating oxygenated blood from the left ventricle into myocardium; positioning a distal end of the perfusion tube in the pathway so as to communicate oxygenated blood from the left ventricle into myocardium, such that during treatment or other medical procedure in which the coronary artery is temporarily occluded, a distal anatomy of the heart is continuously supplied with oxygenated blood; and performing the treatment or other medical procedure in which the coronary artery is temporarily occluded. The method can also comprise the following preliminary step: positioning a laser delivery means or other functional device within the hollow tubular perfusion tube such that a distal end of the laser delivery means or other functional device extends from the distal end of the perfusion tube; and the step of creating a pathway for communicating oxygenated blood from the left ventricle into myocardium is performed using the distal end of the laser delivery means or other functional device. The method can also comprise the following step: removing the laser delivery means or other functional device from the hollow tubular perfusion tube to communicate oxygenated blood from the left ventricle into myocardium.

A transmyocardial revascularization (TMR) enhanced treatment for coronary artery disease and other medical procedures utilizing a perfusing device is also disclosed, the perfusing device having first tubular means for communicating oxygenated blood in the left ventricle with the device and having second tubular means for perfusing oxygenated blood directly into myocardium of the heart muscle, the first tubular means in fluid communication with the second tubular means. The treatment or other medical procedure is one in which a coronary artery is temporarily occluded during a surgical or other procedure. The enhanced treatment comprises the following steps: positioning a distal end of the first tubular means inside the left ventricle; positioning a distal end of the second tubular means inside myocardium of the heart muscle to create at least one TMR channel communicating oxygenated blood from the left ventricle to myocardium, such that during treatment or other medical procedure in which the coronary artery is temporarily occluded during a surgical or other procedure, the heart is continuously supplied with oxygenated blood; and performing the treatment or other medical procedure in which the coronary artery is temporarily occluded during a surgical or other procedure. The second tubular means can have at least one perfusion aperture located on the sidewall adjacent the distal end of the second tubular means and the step of positioning the distal end of the second tubular means inside myocardium can be replaced with the following step: positioning a distal end of the second tubular means inside myocardium of the heart muscle to create at least one TMR channel communicating oxygenated blood from the left ventricle into myocardium of the heart muscle, such that during treatment or other medical procedure in which the coronary artery is temporarily occluded during a surgical or other procedure, the heart is perfused with oxygenated blood. The TMR device can comprise at least one oxygenated blood inlet and at least one oxygenated blood outlet and a pump means for communicating oxygenated blood from the at least one inlet through the at least one outlet, and the method can further comprise the following step: actuating the pump means, thereby enhancing communication of oxygenated blood from the at least one inlet through the at least one outlet. The pump means can be actuated manually or automatically. The step of actuating the pump means can be repeated at least once during the treatment or other medical procedure. The step of actuating the pump means is repeated at a specific rate during the treatment or other medical procedure. The treatment or other medical procedure can be a coronary artery angioplasty, a coronary artery bypass grafting (CABG), or a minimally invasive direct coronary artery bypass grafting (MIDCAB).

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Scope

As mentioned above, the scope of the present invention includes any use of laser energy to create channels, openings or other laser treated areas, such as created in TMR, as a beneficial adjunct therapy to, or supplemental therapy with, procedures for treating heart disease such as coronary artery disease, including CABG and MIDCAB. It will be understood that a complete TMR procedure typically involves creation of a fairly large plurality of TMR channels. However, any use of TMR in conjunction with these types of procedures is considered within the scope of the present invention. Therefore, the present invention is described as being especially useful in conjunction with MIDCAB of the LAD coronary artery, either as an adjunct therapy, i.e. less than a complete TMR, or supplemental with, i.e. with a complete TMR procedure. Furthermore, it will be understood that the invention also includes the use of laser energy to treat any portion of the human body in conjunction with any other primary medical procedure in which the formation of the laser treated area or areas, other openings or other laser treated tissue, enhances or otherwise improves the other primary procedure.

Methodology

Figure 1:
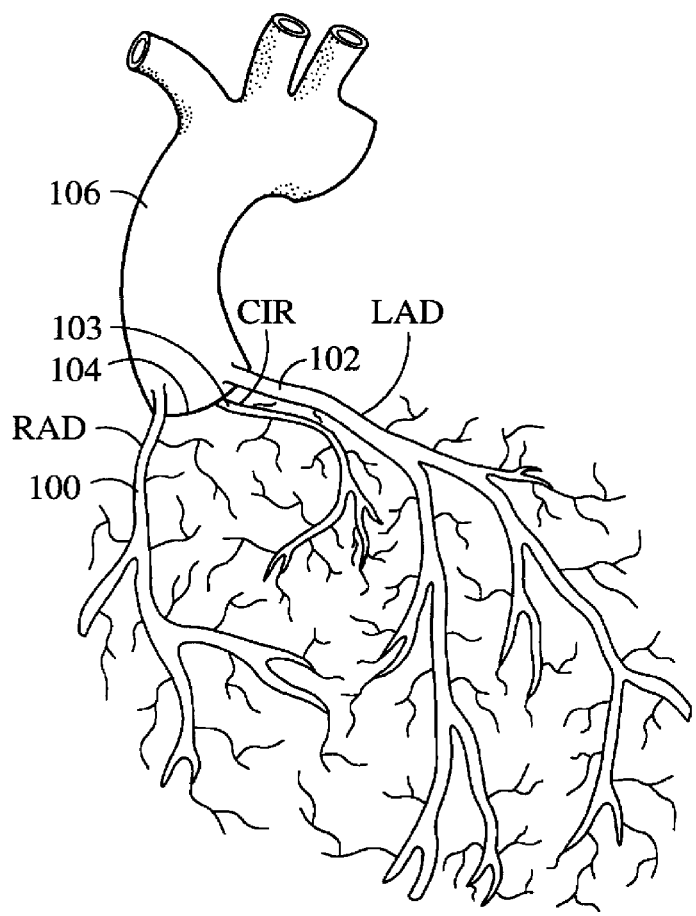
FIG. 1 is a schematic view of the coronary arteries on the outer surface of the human heart.
Figure 3:
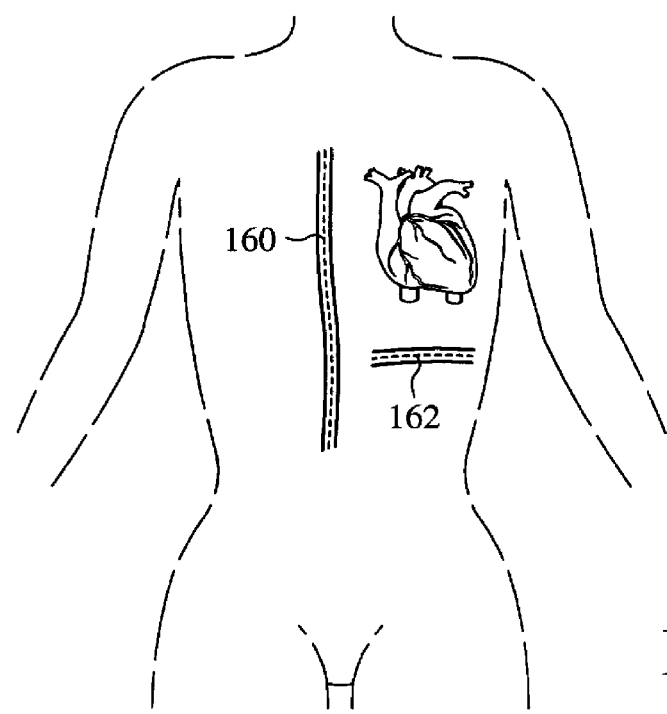
FIG. 3 is a representative drawing showing typical locations of the sternotomy and the thoracotomy incisions.
Figure 2:
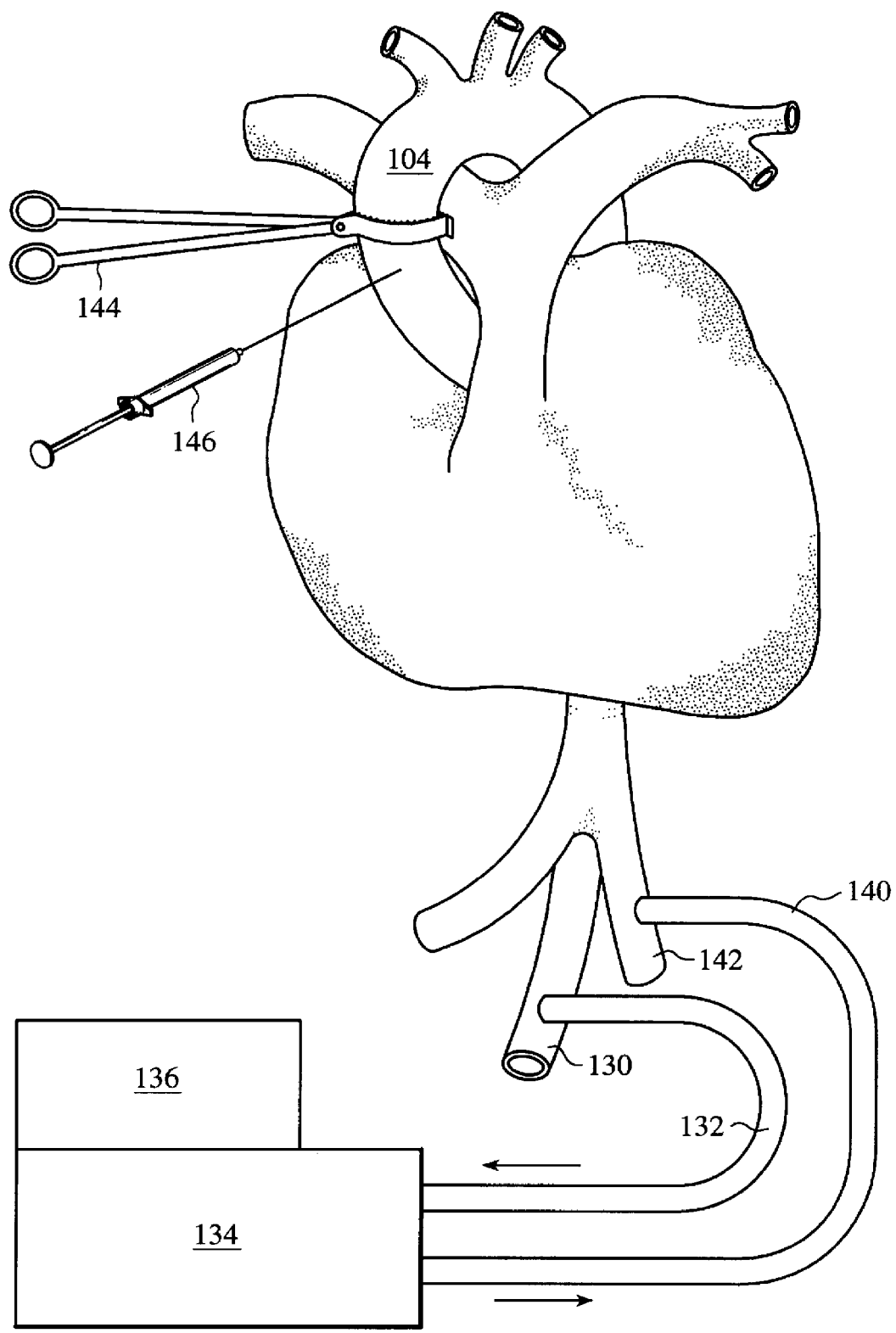
FIG. 2 is a representative schematic view of the use of a cardiopulmonary bypass (CPB) machine.
Figure 4:
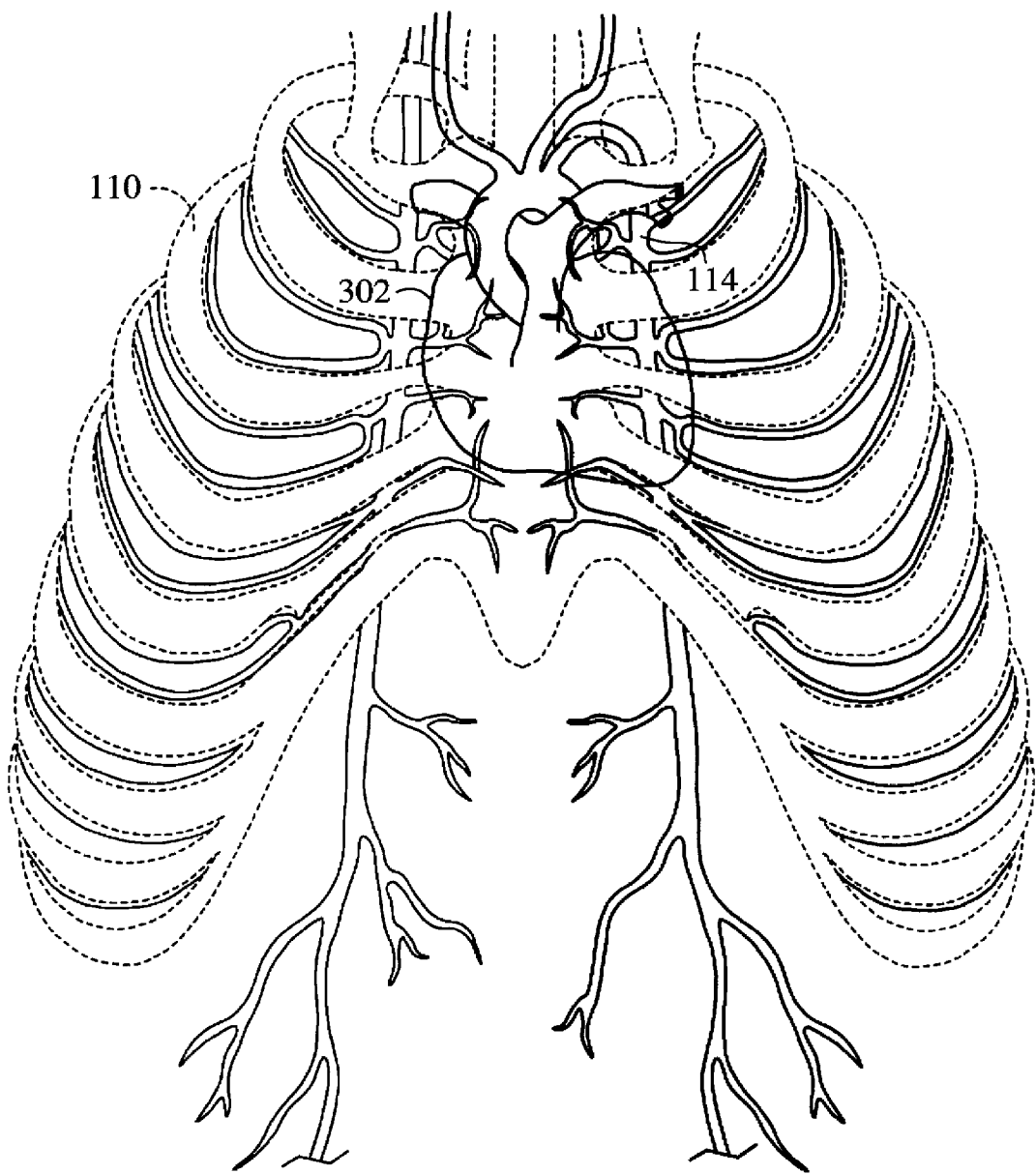
FIG. 4 is a representative drawing showing typical anatomy involved in a LIMA to LAD type of MIDCAB procedure.

FIG. 4 is a representative drawing showing typical anatomy involved in a LIMA to LAD type of MIDCAB procedure. As mentioned above, although the present methodology and apparatus are described with specific reference to TMR in conjunction with a MIDCAB procedure, the scope of the invention includes any TMR in conjunction with any type of bypass grafting procedure.

When a mini-thoracotomy or other MIS procedure, such as by an anterior mediastinotomy approach, is being performed, the costal cartilage 110 is between the heart 302 and the surgeon. Typically either the third or the fourth costal cartilage 110 will be at least partially excised, depending upon the size of the heart 302 and upon the location of the occlusion in the coronary artery. It will be understood that while often it may be necessary to remove a portion of the costal cartilage 110, more skilled or experienced practitioners will be able to perform the procedure without removing any costal cartilage 110, thus reducing the operating procedure duration by as much as 10 to 15 minutes or more. Behind the sternum 112 lies the heart 302.

Figure 5A:
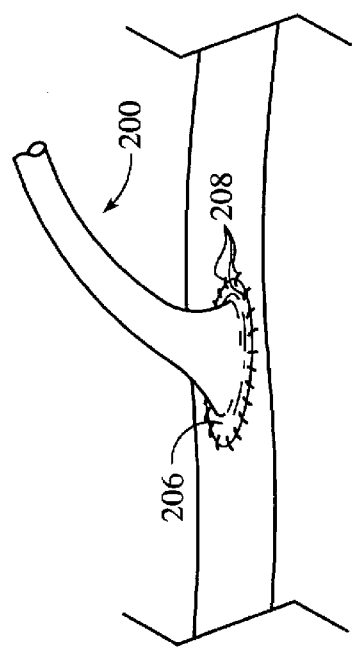
FIGS. 5A and 5B are representative perspective views showing alignment of a portion of a vessel for CABG with an incision in the coronary artery, and the attached portion sewn into place onto the coronary artery, respectively.
Figure 5B:
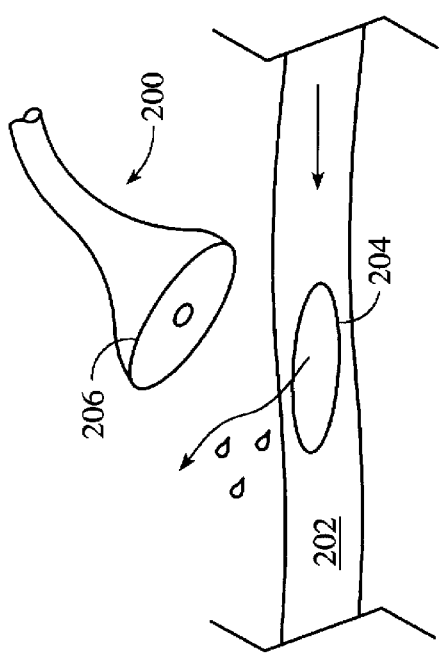
Figure 6A:
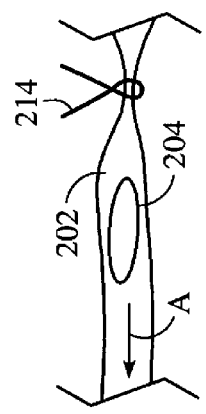
FIGS. 6A, 6B, 6C and 6D show four methods for temporarily blocking blood flow through the coronary artery for performing CABG.
Figure 6B:
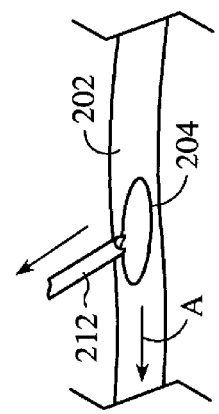
Figure 6C:
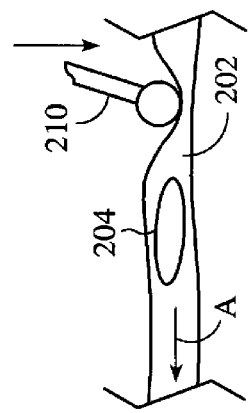
Figure 6D:
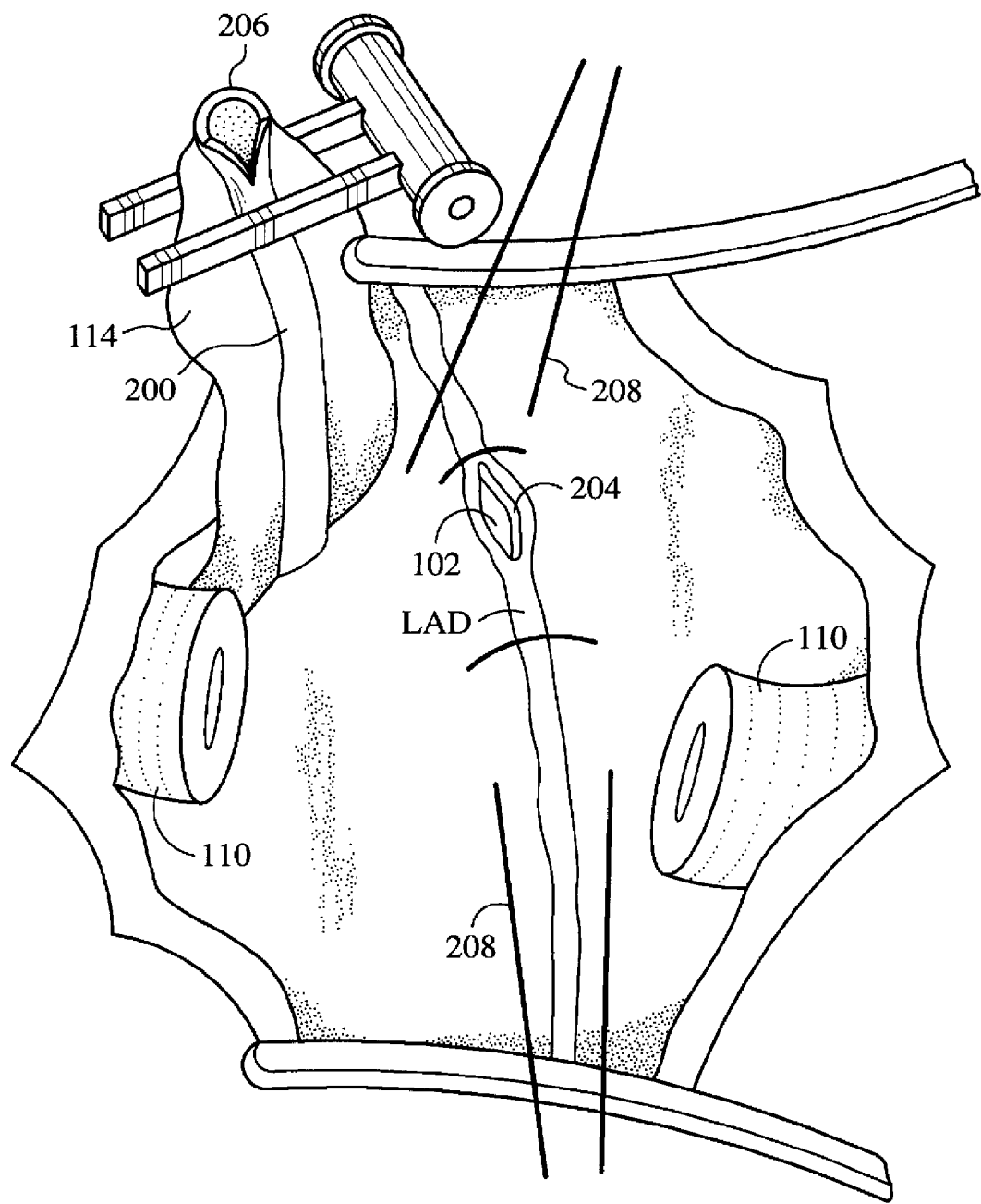

FIGS. 5A and 5B are representative perspective views showing alignment of a portion of a vessel for CABG with an incision in the coronary artery, and the attached portion sewn into place onto the coronary artery, respectively. As described, during the standard CAB procedure, a vessel graft 200 is harvested from another portion of the vasculature. The proximal end, not shown, can be attached directly to the aorta. Alternatively, a portion of LIMA can be used as well. In that case, the vessel to be grafted to the coronary artery 202 can be harvested by removing a portion of the LIMA entirely. Additionally, the LIMA can be severed at only one point somewhat distal from the uppermost portion of the LIMA where it originates adjacent the aorta, and grafted directly to the coronary artery at a point distal to the stenosis or other occlusion.

In any event, once a portion of vessel graft 200 is made available, an incision 204 is made directly in the coronary artery 202 at a point distal to the stenosis or other occlusion. The distal end 206 of the vessel graft 200 is sutured 208 directly to the coronary artery 202 so as to provide communication of oxygenated blood through the vessel graft 200 into the coronary artery 202 directly.

FIGS. 6A, 6B, 6C and 6D show four conventional methods for temporarily blocking, or compensating for, blood flow through the coronary artery for performing CABG. It will be understood that unless the coronary artery is completely blocked, blood flow in direction A will cause blood to flow out of the coronary artery 202 at the point of the incision 204. For this reason, before the vessel graft 200 can be sutured into place, a section of the coronary artery 202 must be occluded. This can be done in a number of ways. In a simple method, the coronary artery 202 can be occluded by exerting pressure across the coronary artery 202 with a blunt instrument 210. Alternatively, a suction tube 212 can be operatively positioned adjacent the incision 204 in the coronary artery 202 to eliminate excessive blood loss in the operative field using a vacuum. A third solution is to clamp the coronary artery with a silastic band 214 or other suitable clamp may also be used.

With the anterior mediastinotomy or other similar MIS approach, care is required during the excision of costal cartilage 110 to avoid injury to the underlying left internal mammary artery (LIMA) 114. Typically a section of LIMA 114 between about 4 and about 12 centimeters is harvested by dissection of the pedicle. After completing dissection, heparin is given and papaverin can be injected into the distal end 206 of the vessel graft 200. A segmentary occlusion of the coronary artery 202, such as on the LAD 102, is formed about 2.5 centimeters long. Two looping sutures 216 can be used to achieve a clean, dry operating field during the anastomy procedure. Once in place, gentle traction of the two stay sutures 216 completes the immobilization of the operative field. At this point, an incision 204 can be made in the coronary artery 202 and the anastomosis or graft, such as LIMA to LAD, is performed. After completing the graft, stay sutures 216 can be removed.

Figure 7A:
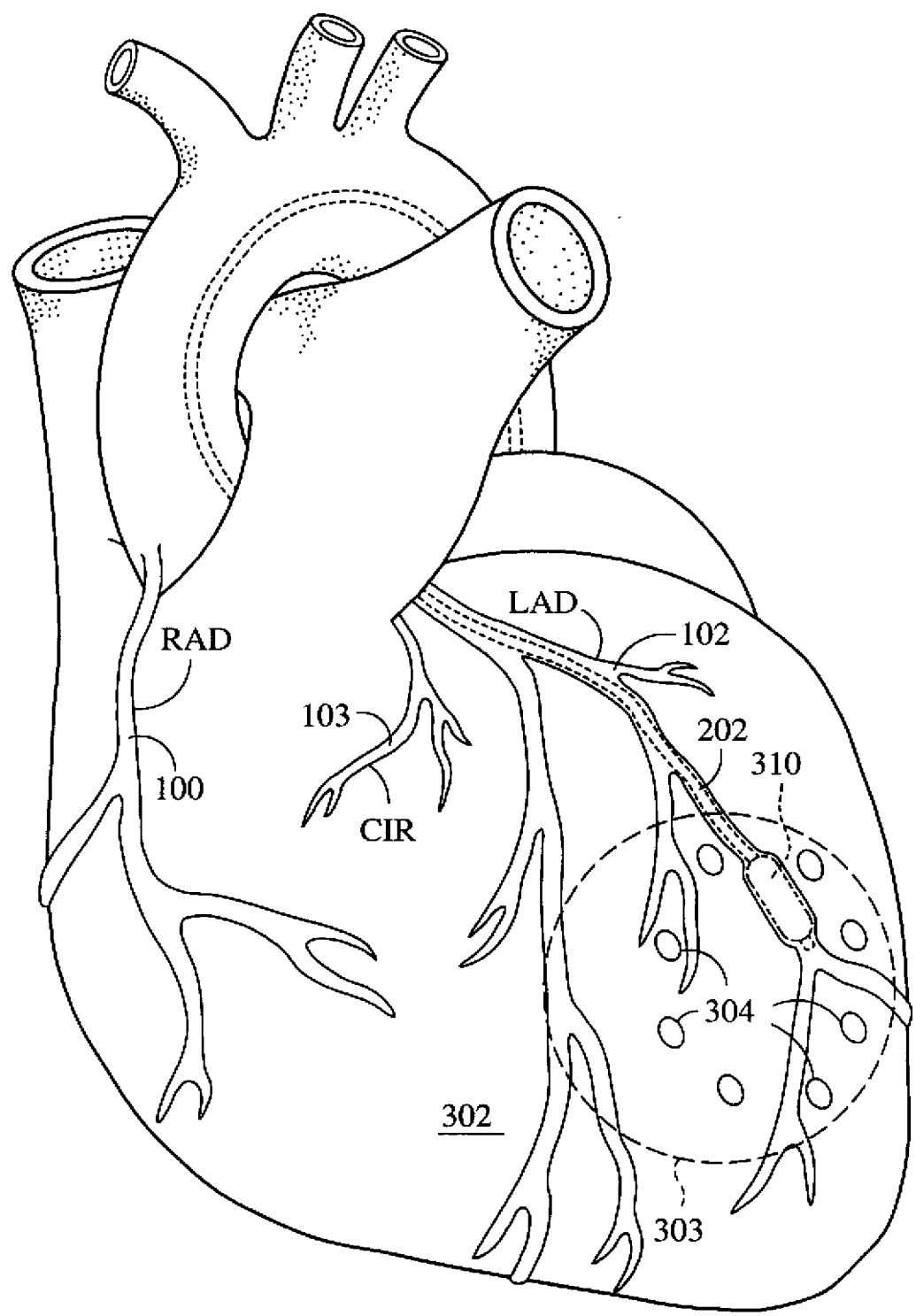
FIGS. 7A and 7B are representative perspective views of a human heart showing placement of TMR channels in the distal heart anatomy to reduce or eliminate the risk of starving the distal heart anatomy of oxygen in conjunction with angioplasty as taught by the present invention.
Figure 7B:
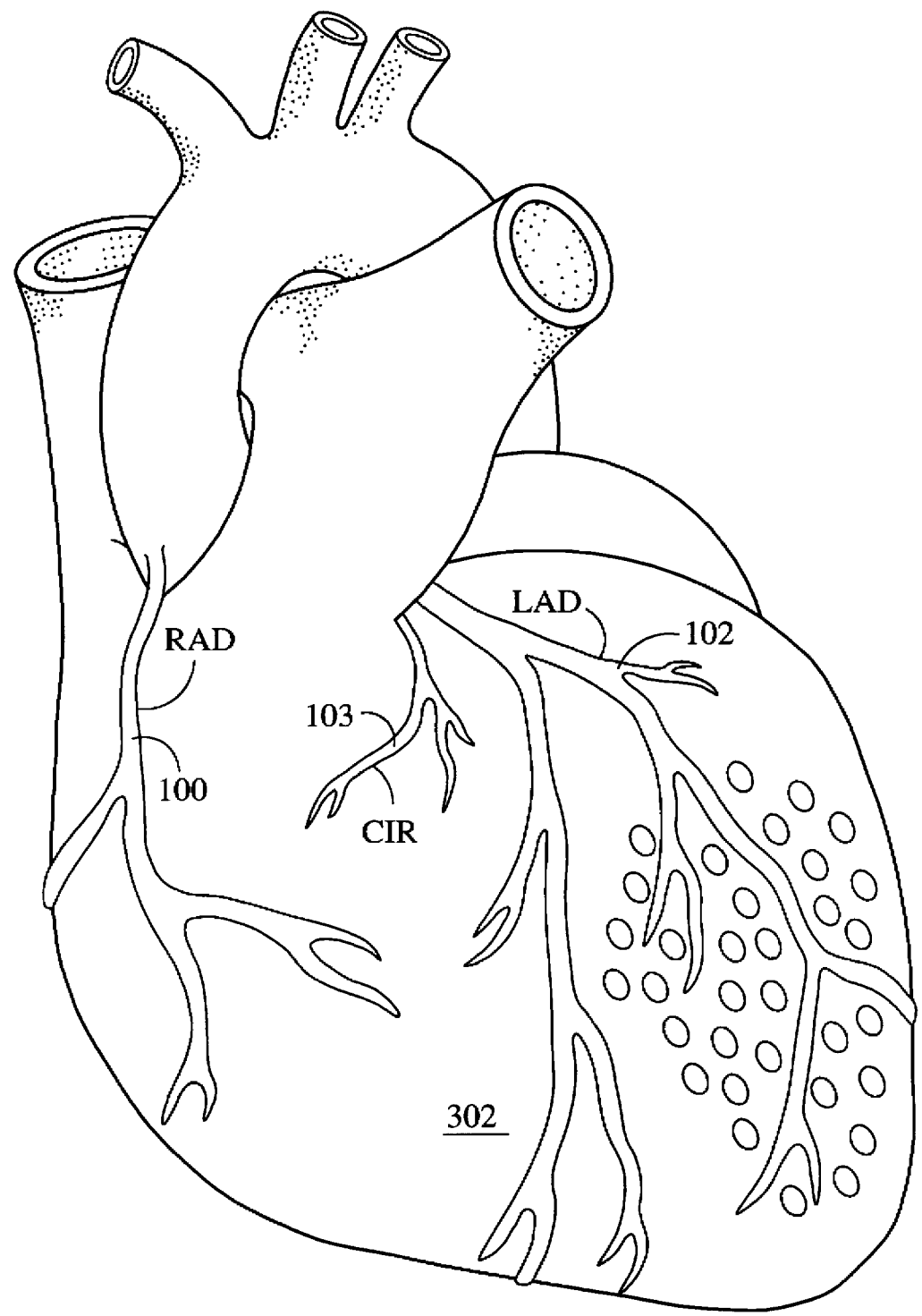
Figure 8A:
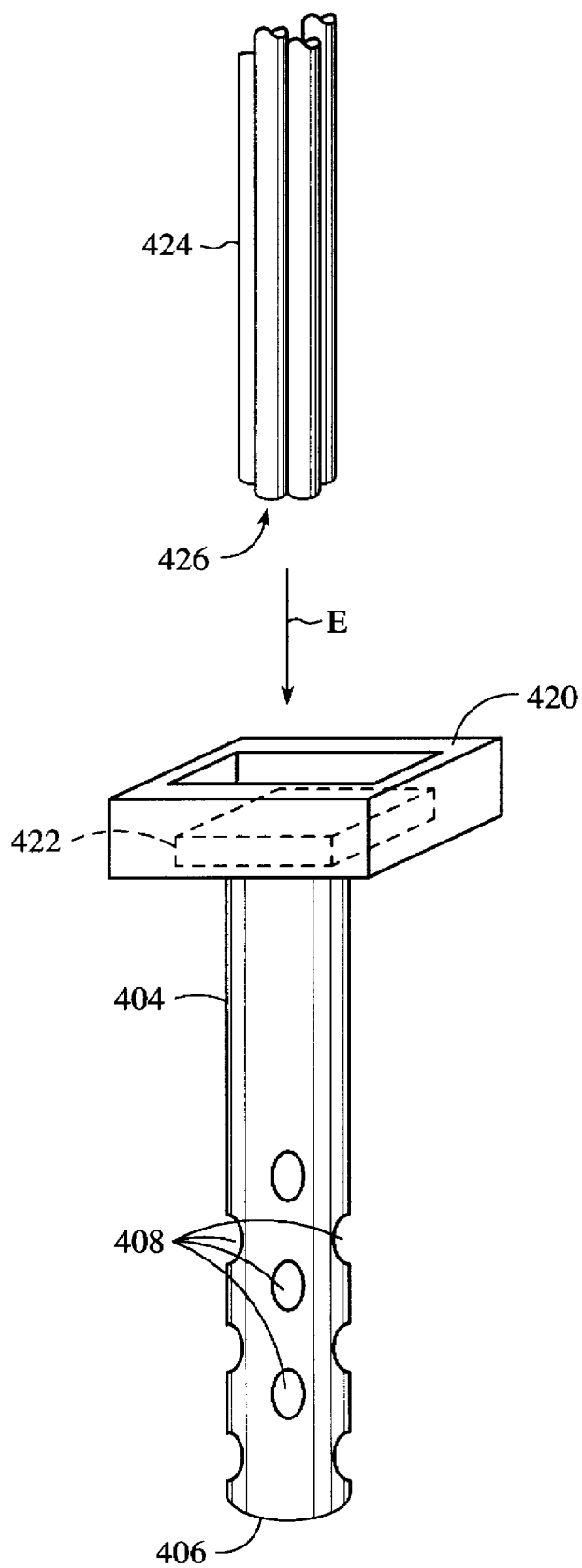
FIGS. 8A–8D are representative perspective views of a TMR perfusion tube 404 and method of use, both of the present invention.
Figure 8B:
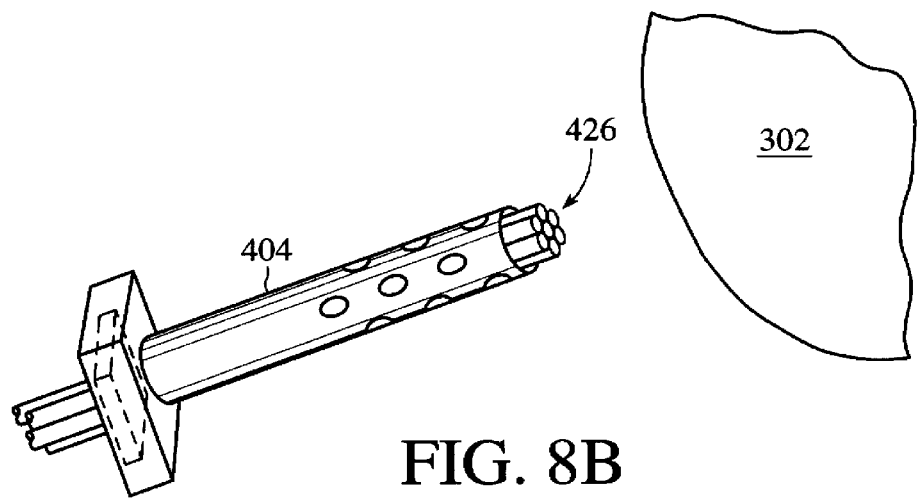
Figure 8C:
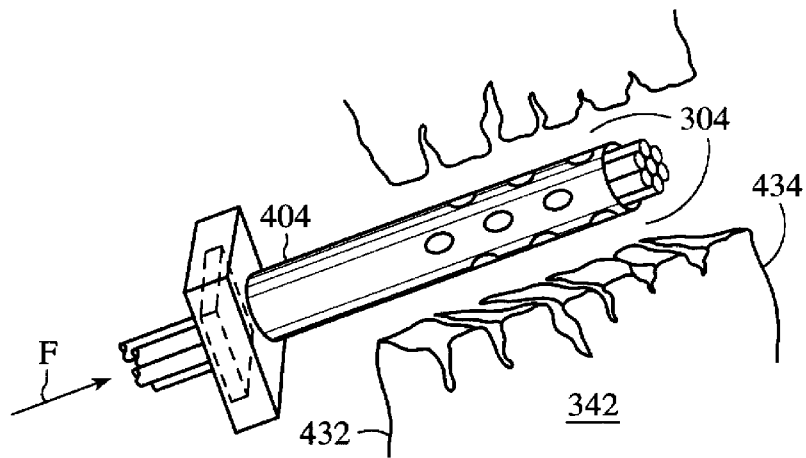
Figure 8D:
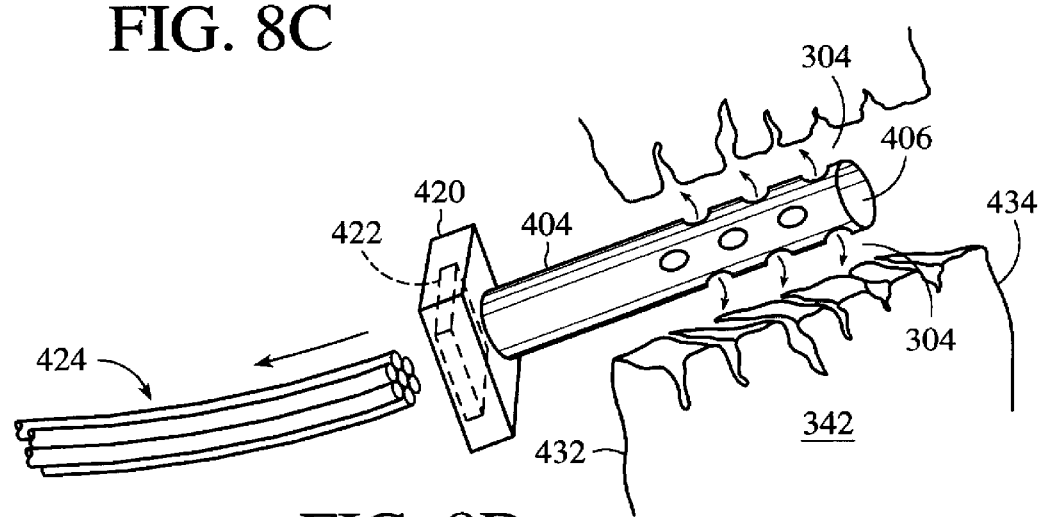

FIGS. 7A and 7B are representative perspective views of a human heart showing placement of TMR channels in the distal heart anatomy to reduce or eliminate the risk of starving the distal heart anatomy of oxygen, in conjunction with angioplasty, as taught by the present invention. As mentioned above, in order to provide the distal anatomy, designated generally as that portion of heart muscle 302 demarcated by dashed line 303, with sufficient oxygen during the angioplasty, CABG, MIDCAB or other coronary artery disease treatment procedure, at least one and preferably a plurality of TMR channels 304 are created. The effect of creating these TMR channels 304 is to revascularize the distal anatomy of the heart muscle 302 and provide sufficient oxygenated blood to that area during the pendency of the intervention. These plurality of TMR channels 304 are preferably created surgically from the epicardial surface through myocardium all the way into the ventricle, and also may be created from inside a ventricle of the heart through endocardium. In this way, the TMR channels 304 act as a natural bypass to shunt blood from the ventricle into at-risk myocardium. The TMR channels 304 remain patent for at least a brief period of time, and in the case of angioplasty, CABG or other MIDCAB procedures, this period of time is at least long enough to perform such procedures safely without the risk of starving the distal anatomy of sufficient oxygen thereby.

As will be understood, FIG. 7A represents the location of TMR channels 304 created in conjunction with balloon angioplasty or other procedures. FIG. 7B shows TMR channels 304 in any non-bypassed risk area. Therefore, the scope of the present invention includes both TMR or other laser treatment both as an adjunct therapy, i.e. with less than a complete TMR, or as supplemental therapy, i.e. with a complete TMR procedure. Further, the method can also be practiced using an ultrasound device and the step of creating a channel comprises creating an opening in the portion of the heart muscle with the ultrasound device. Alternatively, the tool used can be a radio frequency thermal source and the step of creating a channel comprises creating an opening in the portion of the heart muscle with the radio frequency thermal source tool.

As shown, once the plurality of TMR channels 304 have been created, blockage or interruption of blood flow to the coronary artery 202 of interest in the primary intervention can be permitted safely. In one other embodiment of the method of the present invention, an angioplasty balloon 310 interventional catheter is introduced into the coronary artery 202 to reduce an occlusion. It is understood that prior to the present invention, a typical angioplasty procedure could only interrupt blood flow completely through the coronary artery 202 for a brief period of time without a greatly increased risk of heart attack, ischemia or infarction. Other procedures for which TMR will serve as a suitable adjunct therapy include but are not limited to mechanical resection of lesions, CABG and MIDCAB procedures, and any other procedure where it is desirable to temporarily block or interrupt blood flow in a coronary artery. Alternatively, retro-lasing can also be performed using the apparatus and methods of the present invention. This application includes the steps of advancing a fiber or other laser delivery means, with or without a piercing tip, a predetermined distance into the myocardium and then delivering laser energy to create a TMR channel or other treatment site while retracting the fiber, laser delivery means or other functional device. In TMR initiated from endocardial surfaces into myocardium, inasmuch as laser energy is delivered during retraction of the fiber, the possibility of advancing the fiber too far and lasing through the epicardium is eliminated, as are complications arising from such epicardial perforations including but not limited to cardiac tamponade (a buildup in the pericardial sac of an excess of fluid such as blood), proliferation of adhesions, etc.

By the foregoing, it will be recognized by those skilled in the art that the TMR channels provide more than temporary vascular support during cardiovascular procedures. Most such procedures are performed on unhealthy hearts and the long term benefits of TMR are well documented. Additionally, TMR stimulates angiogenesis which would occur coincident with a new blood supply to the area, thereby maximizing angiogenesis.

Apparatus

It will be understood to those skilled in the art that essentially any suitable TMR device will serve for implementing the method of the present invention. Examples of such instruments are more fully described in co-pending U.S. Pat. applications: with regard to surgical and MIS approaches, Ser. No. 08/607,782, now allowed, filed Feb. 27, 1996, Ser. No. 08/675,698, now allowed, filed Jul. 3, 1996 and Ser. No. 08/675,732, now allowed, filed Jul. 3, 1996; and with regard to percutaneous devices or other approaches through the vasculature, Ser. No. 08/627,699 filed Mar.29, 1996, Ser. No. 08/675,732, now allowed filed Jul. 3, 1996, Ser. No. 08/714,243 filed Sep. 3, 1996 and Ser. No.08/714,893 filed Sep. 14, 1996. Additionally, Ser. No. 08/713,531 filed Sep. 13, 1996 teaches a method and apparatus for mechanical TMR of the heart.

In a preferred embodiment of the present invention involving the use of one or more TMR channels or other openings, laser treated areas or mechanically treated areas to increase the supply of oxygenated blood to the distal anatomy, the novel apparatus described below is used. It will be understood that the apparatus described is not required for enhancing blood flow to the distal anatomy via TMR, but will serve as an optional, improved method.

FIGS. 8A–8D are representative perspective views of a TMR perfusion tube 404 and method of use, both of the present invention. The perfusion tube 404 comprises a proximal end 420 and a distal end 406, with one or more blood flow perfusion apertures 408 adjacent the distal end 406. A blood seal means 422 such as an elastomeric or other flexible membrane, hinged or ball valve, etc., will prevent undesired blood flow. As shown, a laser delivery means 424 or other functional device such as those mentioned above, including piercing needles, is inserted into the proximal end 420 of the thin wall perfusion tube 404, in the direction E as shown. The distal end 426 of laser delivery means 424 or other functional device is used to create a TMR channel 304 or other opening in tissue of the heart muscle 302.

In a preferred embodiment, the method includes piercing the heart 302 with the distal end 426 of laser delivery means 424 or other functional device, including needle punch, etc., starting at an epicardial surface 432 and penetrating myocardium 342 to pierce an endocardial surface 434, in direction F as shown. As the TMR channel 304 or other opening is created, the distal end 406 of the perfusion tube 404 is disposed within the heart. After a TMR channel 304 or other opening, laser treated area or mechanically treated area is created, optionally extending all the way through both an epicardial surface and an endocardial surface, as shown, or alternatively through only one of the surfaces, the laser delivery means 424 or other fuctional device is retracted from the hollow tubular perfusion tube 404 completely, leaving the perfusion tube 404 in place. Blood flow through the plurality of perfusion apertures 408 into myocardium adjacent the TMR channel 304 will provide an increased supply of oxygenated blood for the beating heart.

As disclosed, one or more of the perfusion tubes 404 will be placed in the heart of other part of the body in conjunction with or following laser or mechanical treatment. The thin walled, plastic, metal or other suitable tubing material perfusion tube 404 doesn't need to be connected to any type of pump or manifold because, due to the perforations at the distal end 406 of the perfusion tube 404, the device will act like a mini, temporary or permanent stent to perfuse oxygenated blood. A suitable material would be polyethylene or PEBAX tube material of about 0.010 inches wall thickness with about a 1 millimeter clearance inside diameter. The structure of the perfusion tube 404 resists myocardial compression during the cardiac cycle, causing a force which squeezes blood directly into the capillaries of the myocardium 342. Flow rates of blood through these devices is fairly low, however by maintaining at least a slight positive pressure, such as about ≦100 millimeters Hg, and saturating the capillary bed. Any minimum flow will help minimize any risk of hemolysis.

Figure 9:
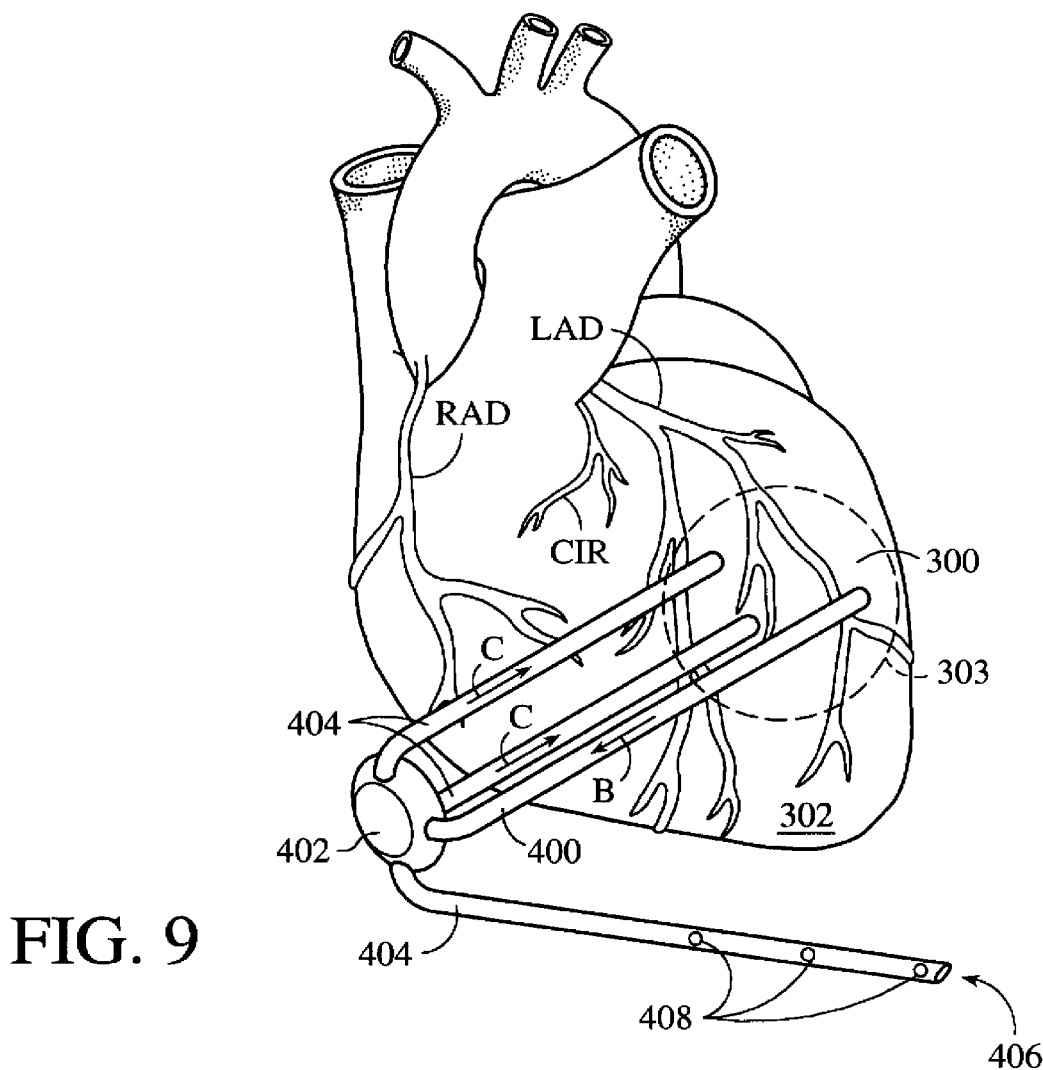
FIG. 9 is a representative perspective view of a TMR device of the present invention for communicating oxygenated blood directly to myocardium to reduce or eliminate the risk of starving the distal heart anatomy of oxygen during coronary artery treatment, including angioplasty and the placement of CAB grafts.

FIG. 9 is a representative perspective view of a TMR perfusion device of the present invention for communicating oxygenated blood directly to myocardium to reduce or eliminate the risk of starving the distal heart anatomy of oxygen during coronary artery treatment, including angioplasty and the placement of CAB grafts. A primary supply tube 400 is inserted into the heart muscle 302 in the vicinity of the distal anatomy. Blood from the left ventricle, flowing in direction B, will flow through the device, entering a manifold 402 in a preferred embodiment, and out of the manifold 402 through at least one perfusion tube 404 adapted for use with the device. These perfusion tubes 404 are inserted into myocardium adjacent the distal anatomy. It will be understood that more than one supply tube 400 can be used as well as more than one perfusion tube 404.

The distal ends 406 of both the supply tube(s) 400 and the perfusion tube(s) 404 preferably are sharpened to mechanically pierce through the epicardium in the distal anatomy with a minimum of trauma to the tissue. The distal ends 406 can be cut at an angle or otherwise optimized for such purposes.

Additionally, with respect to the one or more perfusion tubes 404, a plurality of perfusion apertures 408 can be placed on the sidewalls of the perfusion tubes 404. Thus, blood flowing into the device through supply tube(s) 400 and out of the device in direction C through perfusion tubes 404 will be perfused directly into myocardium through perfusion apertures 408 of perfusion tubes 404.

Figure 10:
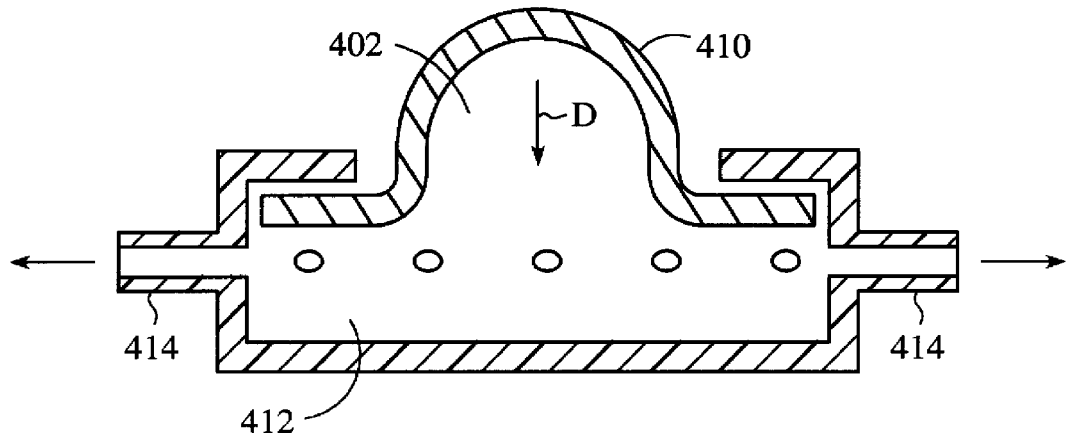
FIG. 10 is a representative section drawing of a TMR device of the present invention.

FIG. 10 is a representative section drawing of a TMR device of the present invention. As described, blood flow through the device follows a path from the ventricle into and through a supply tube 400, to through and out of one or more perfusion tubes 404. In the preferred embodiment shown, blood flows through manifold 402 which serves as a reservoir to equalize, slow and reduce turbulence in blood flow through perfusion tubes 404. It will be understood, however, that said manifold need only be a connection between the exposed ends of the supply tube(s) and the perfusion tubes. In a preferred embodiment of the present invention, the manifold has a pumping mechanism which can be actuated manually or automatically. A rubber dome 410, when depressed in direction D, will collapse into reservoir 412 thereby forcing blood through outlets 414 in direction C. It will be understood that the use of the pumping means to enhance blood flow through the perfusion tubes is an optional improvement over the foregoing described inventions, and the primary supply tube 400 and the perfusion tubes 404 can be joined by a manifold of any type.

Thus, the TMR device acts essentially as a TMR channel itself. Oxygenated blood is communicated directly through the supply tube(s) into myocardium via perfusion apertures and the distal end itself of the perfusion tubes. In a preferred embodiment, as described, oxygenated blood can actually be pumped, either manually or automatically, through the device. This will enhance perfusion (i.e., provide a greater rate of oxygen transfer from the oxygenated blood into the tissue of the myocardium) over direct tubular communication between left ventricle and myocardium. It will be understood, however, that both embodiments are considered within the scope of this invention. Furthermore, with regard to embodiments of TMR devices having pump means, actuation of the pump means can be repeated manually as often as desired. It can also be automatically actuated on a programmed basis, based on dependent or independent parameters including time, heart rate, pressure gradient, peristaltic pressure, flow rate, actual measured oxygen concentration in the distal anatomy of the heart muscle, etc. Additionally, the device of FIG. 9 further may be expected to produce at least temporary TMR channels, thereby contributing to angiogenesis at the treated areas or areas.

It will be understood that the procedure shown in described in the left ventricle, and that the scope of this invention also includes TMR and TMR device use elsewhere in or on the area of the heart 302 affected by the primary procedure.

The TMR portion of the methods and apparatus of the present invention may involve adjunct use of appropriate blood seal means, depth stop apparatus such as clamps, etc., visualization means, marker means as well as other hardware and methodology will be considered within the scope of the present invention. Visualization, particularly for percutaneous, interarterial and MIS based TMR, can be enhanced with ultrasound or by using radio-opaque materials for construction, metal or other material foils or bands, especially at or adjacent distal ends of the outer jacket, the guide tube, and even on the optical fibers. This will assist the practitioner in fluoroscopy or other visualization methodology for precise and accurate positioning of the apparatus and deposit of drug solutions and other substances.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and/or surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like.

Additionally, as described above especially with regard to FIG. 7B, TMR may follow the MIDCAB procedure in non-bypassed areas of myocardium even if bypass protection is not elected in those areas. It will also be understood that the apparatus and method of the present invention as described herein which includes the combination or use with of any conventional mechanism or method which are known to those skilled in the art, are included within the scope of this invention.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. In a heart procedure where blood flow is temporarily halted to at least one coronary artery on a beating heart, the improvement to the procedure is a localized adjunct treatment in combination therewith comprising the steps of:
    a) positioning a tissue removing means adjacent affected myocardial tissue prone to blood-flow deprivation where the blood flow is temporarily halted to the at least one coronary artery; and
    b) forming at least one myocardial revascularizing channel in the affected myocardial tissue using the tissue removal instrument, thereby providing oxygenated blood to and revascularizing the affected myocardial tissue.

2. The procedure of claim 1 wherein in the step b), the tissue removing means provided is a laser energy delivery means for removing the heart tissue.

3. The procedure of claim 2 wherein in the step b), the tissue removing means positioning is at the heart's epicardial surface.

4. The procedure of claim 3 wherein the laser energy delivery means further includes a piercing tip member and the step b) further includes an initial step of mechanically piercing an epicardial surface prior to positioning the laser energy delivery means in myocardial tissue and forming the at least one myocardial revascularizing channel.

5. The procedure of claim 3 wherein the step b) further includes forming additional myocardial revascularizing channels at distal portions of the heart in relation to the at least one coronary artery, thereby providing supplemental treatment.

6. The procedure of claim 2 wherein in the step b), the tissue removing means positioning is at the heart's endocardial surface.

7. The procedure of claim 6 wherein the laser energy delivery means further includes a piercing tip member and the step b) further includes an initial step of mechanically piercing an endocardial surface prior to positioning the laser energy delivery means in myocardial tissue and forming the at least one myocardial revascularizing channel.

8. The procedure of claim 1 wherein in the step b), the tissue removing means provided is a mechanical cutting means for removing the heart tissue.

9. The procedure of claim 1 wherein in the step b), the tissue removing means provided is an ultrasound means for removing the heart tissue.

10. The procedure of claim 1 wherein in the step b), the tissue removing means provided is a radio frequency thermal source means for removing the heart tissue.

11. The procedure of claim 1 wherein the procedure is a coronary artery angioplasty procedure.

12. The procedure of claim 1 wherein the procedure is a coronary artery bypass grafting procedure.

13. The procedure of claim 1 wherein the procedure is a minimally invasive direct coronary artery bypass grafting procedure.

14. In a bypass grafting heart procedure that includes transmyocardial revascularization, the improvement to the procedure is for providing assistance to the heart's grafting location, the procedure comprising the steps of:
    a) positioning a tissue removing means adjacent to affected myocardial tissue of the grafting location;
    b) forming at least one transmyocardial revascularizing channel in the affected myocardial tissue using the tissue removing means, thereby providing oxygenated blood to and revascularizing the affected myocardial tissue when the heart is active; and
    c) performing the coronary bypass grafting at the grafting location.

15. A heart procedural device for a) temporary use on an active heart and b) providing oxygenated blood to myocardial tissue during a heart procedure, the device comprising:
    a perfusion tube with a tissue penetrating distal end portion adapted for inserting into a heart chamber through myocardial tissue, the perfusion tube forming a conduit between the heart chamber and at least one aperture in the perfusion tube's sidewall, the at least one aperture being adapted to supply oxygenated blood directly into the myocardial tissue during the heart procedure, the perfusion tube is adapted to allow passage of a tissue removal instrument through the perfusion tube and sealing means for allowing the formation of myocardial revascularizing channels; and
    sealing means for preventing blood from escaping the heart, the sealing means attaches to the perfusion tube's proximal end.

16. The device of claim 15 wherein the perfusion tube's distal end has a sharpened end for mechanically piercing heart tissue.

17. A heart procedural device for a) temporary use on an active heart and b) providing oxygenated blood to myocardial tissue during a heart procedure, the device comprising:
    at least one perfusion tube forming a conduit with a tissue penetrating distal end portion for inserting at least into myocardial tissue, the at least one perfusion tube's sidewall has at least one aperture adapted to supply oxygenated blood directly into the myocardial tissue during the heart procedure;

at least one supply tube that inserts into a heart chamber; and manifold means for communicating blood between the at least one supply tube and the at least one perfusion tube's proximal end.

18. The device of claim 17 wherein the at least one perfusion tube and the at least one supply tube each have sharpened distal ends for mechanically piercing heart tissue.

19. The device of claim 17 wherein the manifold means further includes means for pumping blood therethrough.

20. A heart procedure wherein blood flow to a coronary artery is temporarily interrupted during the procedure, the procedure including the steps of;
   a) providing means for perfusing blood between a heart chamber and myocardial tissue;
   b) forming at least one tissue channel for communicating oxygenated blood from the heart chamber directly into the myocardial tissue;
   c) positioning a distal end of the means for perfusing blood in the at least one channel thereby providing oxygenated blood from the heart chamber to the myocardial tissue; and
   d) removing the means for perfusing blood after restoring blood flow to the coronary artery, whereby the myocardial tissue is provided with oxygenated blood during the procedure.

21. The procedure of claim 20 wherein the step a) further includes providing and positioning a tissue removal instrument at a distal end of the means for perfusing blood, thereby facilitating channel formation in step b), and removing the tissue removal instrument from the means for perfusing blood.

22. The procedure of claim 21 wherein in the step a), the means for perfusing blood comprises a perfusion tube with a tissue penetrating distal end portion adapted for inserting into the heart chamber through myocardial tissue, the perfusion tube forming a conduit between the heart chamber and at least one aperture in the perfusion tube's sidewall, the at least one aperture provides oxygenated blood directly into the myocardial tissue, and a sealing means for preventing blood from escaping the heart, the sealing means attaches to the perfusion tube's proximal end.

23. The procedure of claim 20 wherein in the step a), the means for perfusing blood comprises at least one perfusion tube forming a conduit with a tissue penetrating distal end portion for inserting at least into myocardial tissue, the at least one perfusion tube's sidewall having at least one aperture for supplying oxygenated blood directly into the myocardial tissue, at least one supply tube that inserts into a heart chamber, and manifold means for communicating blood between the at least one supply tube and the at least one perfusion tube's proximal end.

24. The procedure of claim 23 wherein in step a), the means for perfusing blood further includes pumping means, and the procedure further includes a step of actuating the pumping means thereby enhancing transport of oxygenated blood between the heart chamber and the myocardial tissue.

25. The procedure of claim 24 wherein the step of actuating the blood pumping means is done manually.

26. The procedure of claim 24 wherein the step of actuating the blood pumping means is done automatically.

27. The procedure of claim 24 wherein the step of actuating the blood pumping means is repeated at least once during the procedure.

28. The procedure of claim 24 wherein the step of actuating the blood pumping means is repeated at a specific rate during the procedure.

29. The procedure of claim 20 wherein the procedure is a coronary artery angioplasty procedure.

30. The procedure of claim 20 wherein the procedure is a coronary artery-bypass grafting procedure.

31. The procedure of claim 20 wherein the procedure is a minimally invasive direct coronary artery-bypass grafting procedure.

32. The procedure of claim 20 wherein the procedure further includes a step of forming myocardial revascularizing channels thereby providing supplemental treatment.

33. The procedure of claim 14 wherein the step b) further includes forming additional transmyocardial revascularizing channels at distal portions of the heart in relation to the at least one coronary artery, thereby providing supplemental treatment.

* * * * *